(12) United States Patent
Kieffer

(10) Patent No.: US 7,297,771 B2
(45) Date of Patent: Nov. 20, 2007

(54) POLYPEPTIDES HAVING OPIOID RECEPTOR ACTIVITY

(75) Inventor: Brigitte Kieffer, Strasbourg (FR)

(73) Assignee: Astra Pharma Inc., Ontario (CA)

( * ) Notice: Subject to any disclaimer, the term of this patent is extended or adjusted under 35 U.S.C. 154(b) by 347 days.

(21) Appl. No.: 10/435,655

(22) Filed: May 12, 2003

(65) Prior Publication Data

US 2004/0096940 A1 May 20, 2004

Related U.S. Application Data

(62) Division of application No. 08/432,174, filed as application No. PCT/FR93/01097 on Nov. 8, 1993, now Pat. No. 6,562,587.

(30) Foreign Application Priority Data

Nov. 10, 1992 (FR) .................................. 92 13526

(51) Int. Cl.
C07K 1/00 (2006.01)
C07K 14/00 (2006.01)
C07K 17/00 (2006.01)

(52) U.S. Cl. .................................................... 530/350

(58) Field of Classification Search ..................... None
See application file for complete search history.

(56) References Cited

U.S. PATENT DOCUMENTS

| 5,350,836 A | 9/1994 | Kopchick et al. |
| 5,985,600 A | 11/1999 | Evans et al. |
| 6,432,652 B1 * | 8/2002 | Evans et al. ................. 435/7.2 |

FOREIGN PATENT DOCUMENTS

| JP | 4099797 | 3/1992 |
| WO | 90/00564 | 1/1990 |
| WO | 91/18901 | 12/1991 |
| WO | WO94/04552 | 3/1994 |

OTHER PUBLICATIONS

Evans CJ et al. Science 258 (5090):1952-1955, 1992.*
Wallace et al., Methods in Enzymology, 152:432, 1987.
Kluxen et al., Proc. Natl. Acad. Science, 89, 4618, 1992.
Vukicevic et al., PNAS USA 93:9021-9026, 1996.
Massague J. Cell 49:437-8, 1987.
Pilbeam et al. Bone 14:717-720, 1993.
Skolnick et al. Trends in Biotech. 18:34-39, 2000.
Bork P. Genome Research 10:398-400, 2000.
Doerks et al. Trends in Genetics 14:248-250, 1998.
Smith et al. Nature Biotechnology 15:1222-1223, 1997.
Brenner SE. Trends in Genetics 15:132-133, 1999.
Bork et al. Trends in Genetics 12:425-427, 1996.
Nucleotide alignments of SEQ ID No. 1 and SEQ ID No. 3 of EP 0672139 with, D2 Keiffer (Dec. 1992) sequence L06322/D3 Yasuda (Jul. 1993) sequence L11064/D4 Evans (Dec. 1992) sequence L07271/D5 Keith (Jul. 1993) sequence S65335.
Kieffer, B. L. et al.: "The δ-opioid receptor: Isolation of a cDNA by expression cloning and pharmacological characterization", Proc. Natl. Acad. Sci. USA, vol. 89, pp. 12048-12052, Dec. 1992.
Yasuda, K. et al.: "Cloning and functional comparison of κ and δ opioid receptors from mouse brain", Proc. Natl. Acad. Sci. USA, vol. 90, pp. 6736-6740, Jul. 1993.
Evans, C. J. et al.: "Cloning of a Delta Opioid Receptor by Functional Expression", Science, vol. 258, Dec. 18, 1992, pp. 1952-1955.
Keith, Jr., D.E. et al.: "Characterization and Mapping of a Delta Opioid Receptor Clone From NG108-15 Cells", Proceedings of the Western Pharmacology Society, vol. 36, 1993, pp. 299-306.
Simonin, F. et al.: "The Human δ-Opioid Receptor: Genomic Organization, cDNA Cloning, Functional Expression, and Distribution in Human Brain", Molecular Pharmacology, vol. 46, Dec. 1994, pp. 1015-1021.
Evans et al., "Cloning of a Delta Opioid Receptor by Functional Expressions", Science, vol. 258, Dec. 1992, pp. 1952-1955.
Evans et al., Abstracts, Society for Neuroscience, vol. 18, part 1, p. 21, 16.1, Oct. 25-30, 1992.
Ann et al., "Specific Reduction of δ-Opioid Receptor Binding in Transfected NG108-15 Cells", J. Biol. Chem., vol. 267, No. 11, pp. 7921-7926, 1992.
Loh et al., "Molecular Characterization of Opioid Receptors", Annu. Rev. Pharmacol. Toxicol., vol. 30, pp. 123-147, 1990.
Fujioka, T. et al., "Purification and reconstitution of μ-opioid receptors in liposome", Journal of Chromatography, vol. 597, pp. 429-433, 1992.
Xie, Guo-Xi et al., "Expression cloning of cDNA encoding a seven-helix receptor from human placenta with affinity for opioid ligands", Proc. Natl. Acad. Sci. USA, vol. 89, pp. 4124-4128, May 1992.
Kieffer, B. et al., "The δ-opioid receptor: Isolation of a cDNA by expression cloning and pharmacological characterization", Proc. Natl. Acad. Sci. USA, vol. 89, pp. 12048-12052, Dec. 1992.
Yasuda, K. et al., "Cloning and functional comparison of kappa and delta opioid receptors from mouse brain", Proc. Natl. Acad. Sci. USA, vol. 90, pp. 6736-6740, Jul. 1993.

* cited by examiner

Primary Examiner—Robert S. Landsman
(74) Attorney, Agent, or Firm—Young & Thompson (57) ABSTRACT

The present invention concerns novel polypeptides having opioid receptor activity, the genetic material permitting their expression, recombinant cells expressing these polypeptides, and their use.

2 Claims, 3 Drawing Sheets

SEQUENCE LISTING

<160> NUMBER OF SEQ ID NOS: 4

<210> SEQ ID NO 1
<211> LENGTH: 2219
<212> TYPE: DNA
<213> ORGANISM: Mus sp.
<220> FEATURE:
<221> NAME/KEY: CDS
<222> LOCATION: (59)..(1174)

<400> SEQUENCE: 1

```
ctctaaaggc tgggtccctg cgcccagggc gcacggtgga gacggacacg gcggcgcc         58 atg gag ctg gtg ccc tct gcc cgt gcg gag ctg cag tcc tcg ccc ctc        106
Met Glu Leu Val Pro Ser Ala Arg Ala Glu Leu Gln Ser Ser Pro Leu
1               5                   10                  15 gtc aac ctc tcg gac gcc ttt ccc agc gcc ttc ccc agc gcg ggc gcc        154
Val Asn Leu Ser Asp Ala Phe Pro Ser Ala Phe Pro Ser Ala Gly Ala
            20                  25                  30 aat gcg tcg ggg tcg ccg gga gcc cgt agt gcc tcg tcc ctc gcc cta        202
Asn Ala Ser Gly Ser Pro Gly Ala Arg Ser Ala Ser Ser Leu Ala Leu
        35                  40                  45 gcc atc gcc atc acc gcg ctc tac tcg gct gtg tgc gca gtg ggg ctt        250
Ala Ile Ala Ile Thr Ala Leu Tyr Ser Ala Val Cys Ala Val Gly Leu
    50                  55                  60 ctg ggc aac gtg ctc gtc atg ttt ggc atc gtc cgg tac acc aaa ttg        298
Leu Gly Asn Val Leu Val Met Phe Gly Ile Val Arg Tyr Thr Lys Leu
65                  70                  75                  80 aag acc gcc acc aac atc tac atc ttc aat ctg gct ttg gct gat gcg        346
Lys Thr Ala Thr Asn Ile Tyr Ile Phe Asn Leu Ala Leu Ala Asp Ala
                85                  90                  95 ctg gcc acc agc acg ctg ccc ttc cag agc gcc aag tac ttg atg gaa        394
Leu Ala Thr Ser Thr Leu Pro Phe Gln Ser Ala Lys Tyr Leu Met Glu
            100                 105                 110 acg tgg ccg ttt ggc gag ctg ctg tgc aag gct gtg ctc tcc att gac        442
Thr Trp Pro Phe Gly Glu Leu Leu Cys Lys Ala Val Leu Ser Ile Asp
        115                 120                 125 tac tac aac atg ttc act agc atc ttc acc ctc acc atg atg agc gtg        490
Tyr Tyr Asn Met Phe Thr Ser Ile Phe Thr Leu Thr Met Met Ser Val
    130                 135                 140 gac cgc tac att gct gtc tgc cat cct gtc aaa gcc ctg gac ttc cgg        538
Asp Arg Tyr Ile Ala Val Cys His Pro Val Lys Ala Leu Asp Phe Arg
145                 150                 155                 160 aca cca gcc aag gcc aag ctg atc aat ata tgc atc tgg gtc ttg gct        586
Thr Pro Ala Lys Ala Lys Leu Ile Asn Ile Cys Ile Trp Val Leu Ala
                165                 170                 175
```

```
tca ggt gtc ggg gtc ccc atc atg gtc atg gca gtg acc caa ccc cgg      634
Ser Gly Val Gly Val Pro Ile Met Val Met Ala Val Thr Gln Pro Arg
            180                 185                 190 gat ggt gca gtg gta tgc atg ctc cag ttc ccc agt ccc agc tgg tac      682
Asp Gly Ala Val Val Cys Met Leu Gln Phe Pro Ser Pro Ser Trp Tyr
            195                 200                 205 tgg gac act gtg acc aag atc tgc gtg ttc ctc ttt gcc ttc gtg gtg      730
Trp Asp Thr Val Thr Lys Ile Cys Val Phe Leu Phe Ala Phe Val Val
    210                 215                 220 ccg atc ctc atc atc acg gtg tgc tat ggc ctc atg cta ctg cgc ctg      778
Pro Ile Leu Ile Ile Thr Val Cys Tyr Gly Leu Met Leu Leu Arg Leu
225                 230                 235                 240 cgc agc gtg cgt ctg ctg tcc ggt tcc aag gag aag gac cgc agc ctg      826
Arg Ser Val Arg Leu Leu Ser Gly Ser Lys Glu Lys Asp Arg Ser Leu
                245                 250                 255 cgg cgc atc acg cgc atg gtg ctg gtg gtg gtg ggc gcc ttc gtg gtg      874
Arg Arg Ile Thr Arg Met Val Leu Val Val Val Gly Ala Phe Val Val
            260                 265                 270 tgc tgg gcg ccc atc cac atc ttc gtc atc gtc tgg acg ctg gtg gac      922
Cys Trp Ala Pro Ile His Ile Phe Val Ile Val Trp Thr Leu Val Asp
            275                 280                 285 atc aat cgg cgc gac cca ctt gtg gtg gcc gca ctg cac ctg tgc att      970
Ile Asn Arg Arg Asp Pro Leu Val Val Ala Ala Leu His Leu Cys Ile
        290                 295                 300 gcg ctg ggc tac gcc aac agc agc ctc aac ccg gtt ctc tac gcc ttc     1018
Ala Leu Gly Tyr Ala Asn Ser Ser Leu Asn Pro Val Leu Tyr Ala Phe
305                 310                 315                 320 ctg gac gag aac ttc aag cgc tgc ttc cgc cag ctc tgt cgc acg ccc     1066
Leu Asp Glu Asn Phe Lys Arg Cys Phe Arg Gln Leu Cys Arg Thr Pro
                325                 330                 335 tgc ggc cgc caa gaa ccc ggc agt ctc cgt cgt ccc cgc cag gcc acc     1114
Cys Gly Arg Gln Glu Pro Gly Ser Leu Arg Arg Pro Arg Gln Ala Thr
            340                 345                 350 acg cgt gag cgt gtc act gcc tgc acc ccc tcc gac ggc ccg ggc ggt     1162
Thr Arg Glu Arg Val Thr Ala Cys Thr Pro Ser Asp Gly Pro Gly Gly
            355                 360                 365 ggc gct gcc gcc tgacctaccc gaccttcccc ttaaacgccc ctcccaagtg         1214
Gly Ala Ala Ala
        370 aagtgatcca gaggccacac cgagctccct gggaggctgt ggccaccacc aggacagcta   1274 gaattgggcc tgcacagagg ggaggcctcc tgtggggacg gggcctgagg gatcaaaggc   1334 tccaggttgg aacggtgggg gtgaggaagc agagctggtg attcctaaac tgtatccatt   1394 agtaaggcct ctccaatggg acagagcctc cgccttgaga taacatcggg ttctggcctt   1454 tttgaacacc cagctccagt ccaagaccca aggattccag ctccaggaac caggaggggc   1514 agtgatgggg tcgatgattt ggtttggctg agagtcccag catttgtgtt atggggagga   1574 tctctcatct tagagaagat aaggggacag ggcattcagg caaggcagct ggggttttgg   1634 tcaggagata agcgcccct tcccttgggg ggaggataag tggggatgg tcaacgttgg     1694 agaagagtca aagttctcac cacctttcta actactcagc taaactcgtt gaggctaggg   1754 ccaacgtgac ttctctgtag agaggataca agccgggcct gatgggcag gcctgtgtaa    1814 tcccagtcat agtggaggct gaggctggaa aattaaggac caacagcctg gcaatttag    1874 tgtctcaaaa taaatgtaa agagggctgg gaatgtagct cagtggtagg gtgtttgtgt    1934 gaggctctgg gatcaataag acaaaacaac caaccaacca aaaaccttcc aaacaacaaa   1994 accaacccct caaaccaaaaa actatgtggg tgtctctgag tctggtttga agagaacccg  2054
```

```
cagccctgta tccctgtggg gctgtggaca gtgggcagaa gcagaggctc cctggatcct    2114
gaacaagggc cccaaaagca agttctaaag ggacccctga aaccgagtaa gcctttgtgt    2174
caagaagtgg gagtacaacc agaaaggtgg ctgagtgctt tagag                    2219
```

<210> SEQ ID NO 2
<211> LENGTH: 372
<212> TYPE: PRT
<213> ORGANISM: Mus sp.

<400> SEQUENCE: 2

```
Met Glu Leu Val Pro Ser Ala Arg Ala Glu Leu Gln Ser Ser Pro Leu
1               5                   10                  15

Val Asn Leu Ser Asp Ala Phe Pro Ser Ala Phe Pro Ser Ala Gly Ala
            20                  25                  30

Asn Ala Ser Gly Ser Pro Gly Ala Arg Ser Ala Ser Ser Leu Ala Leu
        35                  40                  45

Ala Ile Ala Ile Thr Ala Leu Tyr Ser Ala Val Cys Ala Val Gly Leu
    50                  55                  60

Leu Gly Asn Val Leu Val Met Phe Gly Ile Val Arg Tyr Thr Lys Leu
65                  70                  75                  80

Lys Thr Ala Thr Asn Ile Tyr Ile Phe Asn Leu Ala Leu Ala Asp Ala
                85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Gln Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285

Ile Asn Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Thr Pro
                325                 330                 335

Cys Gly Arg Gln Glu Pro Gly Ser Leu Arg Arg Pro Arg Gln Ala Thr
```

```
              340                 345                 350
Thr Arg Glu Arg Val Thr Ala Cys Thr Pro Ser Asp Gly Pro Gly Gly
            355                 360                 365

Gly Ala Ala Ala
        370

<210> SEQ ID NO 3
<211> LENGTH: 998
<212> TYPE: DNA
<213> ORGANISM: Homo sapiens
<220> FEATURE:
<221> NAME/KEY: CDS
<222> LOCATION: (1)..(996)
<220> FEATURE:
<221> NAME/KEY: modified_base
<222> LOCATION: (922)
<223> OTHER INFORMATION: a, t, c, g, other or unknown
<220> FEATURE:
<221> NAME/KEY: modified_base
<222> LOCATION: (927)
<223> OTHER INFORMATION: a, t, c, g, other or unknown
<220> FEATURE:
<221> NAME/KEY: modified_base
<222> LOCATION: (931)..(932)
<223> OTHER INFORMATION: a, t, c, g, other or unknown

<400> SEQUENCE: 3 cgg agc gcc tcg tcc ctc gcc ctg gca atc gcc atc acc gcg ctc tac        48
Arg Ser Ala Ser Ser Leu Ala Leu Ala Ile Ala Ile Thr Ala Leu Tyr
1               5                   10                  15 tcg gcc gtg tgc gcc gtg ggg ctg ctg ggc aac gtg ctt gtc atg ttc        96
Ser Ala Val Cys Ala Val Gly Leu Leu Gly Asn Val Leu Val Met Phe
            20                  25                  30 ggc atc gtc cgg tac act aag atg aag acg acc acc aag atc tac atc       144
Gly Ile Val Arg Tyr Thr Lys Met Lys Thr Thr Thr Lys Ile Tyr Ile
        35                  40                  45 ttc aac ctg gcc tta gcc gat gcg ctg gcc acc agc acg ctg cct ttc       192
Phe Asn Leu Ala Leu Ala Asp Ala Leu Ala Thr Ser Thr Leu Pro Phe
    50                  55                  60 cag agt gcc aag tac ctg atg gag acg tgg ccc ttc ggc gag ctg ctc       240
Gln Ser Ala Lys Tyr Leu Met Glu Thr Trp Pro Phe Gly Glu Leu Leu
65                  70                  75                  80 tgc aag gct gtg ctc tcc atc gac tac tac aat atg ttc acc agc atc       288
Cys Lys Ala Val Leu Ser Ile Asp Tyr Tyr Asn Met Phe Thr Ser Ile
                85                  90                  95 ttc acg ctc acc atg atg agt gtt gac cgc tac atc gct gtc tgc cac       336
Phe Thr Leu Thr Met Met Ser Val Asp Arg Tyr Ile Ala Val Cys His
            100                 105                 110 cct gtc aag gcc ctg gac ttc cgc acg cct gcc aag gcc aag ctg atc       384
Pro Val Lys Ala Leu Asp Phe Arg Thr Pro Ala Lys Ala Lys Leu Ile
        115                 120                 125 aac atc tgt atc tgg gtc ctg gcc tca ggc gtt ggc gtg ccc atc atg       432
Asn Ile Cys Ile Trp Val Leu Ala Ser Gly Val Gly Val Pro Ile Met
    130                 135                 140 gtc atg gct gtg acc cgt ccc cgg gtg ggg gca gtg gtg tgc atg ctc       480
Val Met Ala Val Thr Arg Pro Arg Val Gly Ala Val Val Cys Met Leu
145                 150                 155                 160 cag ttc ccc agc ccc agc tgg tac tgg gac acg gtg acc aag atc tgc       528
Gln Phe Pro Ser Pro Ser Trp Tyr Trp Asp Thr Val Thr Lys Ile Cys
                165                 170                 175 gtg ttc ctc ttc gcc ttc gtg gtg ccc atc ctc atc atc acc gtg tgc       576
Val Phe Leu Phe Ala Phe Val Val Pro Ile Leu Ile Ile Thr Val Cys
            180                 185                 190
```

-continued

| | | | | | | | | | | | | | | | | |
|---|---|---|---|---|---|---|---|---|---|---|---|---|---|---|---|---|
| tat | ggc | ctc | atg | ctg | ctg | cgc | ctg | cgc | agt | gtg | cgc | ctg | ctg | tcg | ggc | 624 |
| Tyr | Gly | Leu | Met | Leu | Leu | Arg | Leu | Arg | Ser | Val | Arg | Leu | Leu | Ser | Gly | |
| | | 195 | | | | 200 | | | | | 205 | | | | | |

```
tcc aag gag aag gac cgc agc ctg cgg cgc atc acg cgc atg gtg ctg     672
Ser Lys Glu Lys Asp Arg Ser Leu Arg Arg Ile Thr Arg Met Val Leu
        210                 215                 220 gtg gtt gtg ggc gcc ttc gtg gtg tgt tgg gcg ccc atc cac atc ttc     720
Val Val Val Gly Ala Phe Val Val Cys Trp Ala Pro Ile His Ile Phe
225                 230                 235                 240 gtc atc gtc tgg acg ctg gtg gac atc aac cgg cgc gac ccg ctg gtg     768
Val Ile Val Trp Thr Leu Val Asp Ile Asn Arg Arg Asp Pro Leu Val
                245                 250                 255 gtg gct cgg ctg cac ctg tgc atc gcg ctg ggt tac gcc aat agc agc     816
Val Ala Arg Leu His Leu Cys Ile Ala Leu Gly Tyr Ala Asn Ser Ser
            260                 265                 270 ctc aac ccc gtg ctc tac gct ttc ctc gac gag aac ttc aag cgc tgc     864
Leu Asn Pro Val Leu Tyr Ala Phe Leu Asp Glu Asn Phe Lys Arg Cys
        275                 280                 285 ttc cgc cag ctc tgt cgc aag ccc tgc ggc cgc cca gac ccc agc agc     912
Phe Arg Gln Leu Cys Arg Lys Pro Cys Gly Arg Pro Asp Pro Ser Ser
290                 295                 300 ttc agc cgc ncc cgn aag nnc acg gcc cgc gag cgt gtc acc gcc tgc     960
Phe Ser Arg Xaa Xaa Lys Xaa Thr Ala Arg Glu Arg Val Thr Ala Cys
305                 310                 315                 320 acc ccg tcc gat ggt ccc ggc ggt ggc gct gcc gcc tg                   998
Thr Pro Ser Asp Gly Pro Gly Gly Gly Ala Ala Ala
                325                 330
```

<210> SEQ ID NO 4
<211> LENGTH: 332
<212> TYPE: PRT
<213> ORGANISM: Homo sapiens
<220> FEATURE:
<221> NAME/KEY: MOD_RES
<222> LOCATION: (308)..(309)
<223> OTHER INFORMATION: any amino acid
<220> FEATURE:
<221> NAME/KEY: MOD_RES
<222> LOCATION: (311)
<223> OTHER INFORMATION: any amino acid

<400> SEQUENCE: 4

```
Arg Ser Ala Ser Ser Leu Ala Leu Ala Ile Ala Ile Thr Ala Leu Tyr
1               5                   10                  15

Ser Ala Val Cys Ala Val Gly Leu Leu Gly Asn Val Leu Val Met Phe
            20                  25                  30

Gly Ile Val Arg Tyr Thr Lys Met Lys Thr Thr Thr Lys Ile Tyr Ile
        35                  40                  45

Phe Asn Leu Ala Leu Ala Asp Ala Leu Ala Thr Ser Thr Leu Pro Phe
    50                  55                  60

Gln Ser Ala Lys Tyr Leu Met Glu Thr Trp Pro Phe Gly Glu Leu Leu
65                  70                  75                  80

Cys Lys Ala Val Leu Ser Ile Asp Tyr Tyr Asn Met Phe Thr Ser Ile
                85                  90                  95

Phe Thr Leu Thr Met Met Ser Val Asp Arg Tyr Ile Ala Val Cys His
            100                 105                 110

Pro Val Lys Ala Leu Asp Phe Arg Thr Pro Ala Lys Ala Lys Leu Ile
        115                 120                 125

Asn Ile Cys Ile Trp Val Leu Ala Ser Gly Val Gly Val Pro Ile Met
    130                 135                 140
```

-continued

```
Val Met Ala Val Thr Arg Pro Arg Val Gly Ala Val Val Cys Met Leu
145                 150                 155                 160

Gln Phe Pro Ser Pro Ser Trp Tyr Trp Asp Thr Val Thr Lys Ile Cys
            165                 170                 175

Val Phe Leu Phe Ala Phe Val Val Pro Ile Leu Ile Ile Thr Val Cys
            180                 185                 190

Tyr Gly Leu Met Leu Leu Arg Leu Arg Ser Val Arg Leu Leu Ser Gly
            195                 200                 205

Ser Lys Glu Lys Asp Arg Ser Leu Arg Arg Ile Thr Arg Met Val Leu
            210                 215                 220

Val Val Val Gly Ala Phe Val Val Cys Trp Ala Pro Ile His Ile Phe
225                 230                 235                 240

Val Ile Val Trp Thr Leu Val Asp Ile Asn Arg Arg Asp Pro Leu Val
                245                 250                 255

Val Ala Arg Leu His Leu Cys Ile Ala Leu Gly Tyr Ala Asn Ser Ser
            260                 265                 270

Leu Asn Pro Val Leu Tyr Ala Phe Leu Asp Glu Asn Phe Lys Arg Cys
            275                 280                 285

Phe Arg Gln Leu Cys Arg Lys Pro Cys Gly Arg Pro Asp Pro Ser Ser
    290                 295                 300

Phe Ser Arg Xaa Xaa Lys Xaa Thr Ala Arg Glu Arg Val Thr Ala Cys
305                 310                 315                 320

Thr Pro Ser Asp Gly Pro Gly Gly Ala Ala Ala
                325                 330
```

POLYPEPTIDES HAVING OPIOID RECEPTOR ACTIVITY

This application is a division of application Ser. No. 08/432,174, filed on May 10, 1995 now U.S. Pat. No. 6,562,587. Application Ser. No. 08/432,174 is the national phase of PCT International Application No. PCT/FR93/01097 filed on Nov. 8, 1993 under 35 U.S.C. § 371. The entire contents of each of the above-identified applications are hereby incorporated by reference.

The present invention relates to novel polypeptides and to the genetic material which enables them to be expressed. More specifically, it relates to novel polypeptides having an opioid receptor activity.

The opioid receptors have been known for a long time as membrane receptors of the nervous system, which receptors mediate the analgesic effects of alkaloid derivatives of opium. Endogenous ligands of these receptors and their precursors have been characterized, and their role in the response to pain and stress has been widely studied (Akil et al., (1984) Annu. Rev. Neurosci. 7, 223-255). Furthermore, pharmacological studies have revealed the existence of three subtypes of opioid receptors: mu (morphine), delta (enkephalin) and kappa (dynorphin) receptors. These same studies also demonstrated that the inhibitory action of the cellular activity of these receptors was linked to the activation of G proteins (Simonds, W. F. (1988) Endocrine Rev. 9, 200-212). For this reason, these receptors are nowadays classified within the family of receptors which interact with G proteins, that is a class of receptors possessing seven transmembrane domains and encompassing approximately 80% of known receptors.

Different laboratories have attempted to clone genes encoding opioid receptors. In particular, a protein which binds opioids with a selectivity of the mu type was purified from ox brain and partially sequenced. A cDNA was then isolated using nucleotide probes derived from this partial sequence. However, the protein which is deduced from this sequence does not possess any transmembrane domain and exhibits a high degree of homology with NCAM, an adhesion molecule (Schofield et al., (1989) EMBO J. 8, 489-495). More recently, the isolation of another cDNA has been described (Xie et al., (1992) Proc. Natl. Acad. Sci. USA 89, 4124-4128), which was obtained by expression cloning. The cDNA library was constructed from human placenta, which only expressed the kappa subtype, and it was screened using a peptide derivative of dynorphin by means of an affinity enrichment technique. However, this protein possesses a relatively weak affinity for opioid ligands, does not exhibit any subtype specificity, and, finally, seems very similar to the receptor for neuromedin K. Finally, all the attempts to clone opioid receptors by PCR, which are based on homologies with receptors coupled to G proteins, have been fruitless.

The present invention describes, for the first time, the cloning of genes encoding opioid receptors. The present invention also describes, for the first time, the sequence of opioid receptors and their expression in recombinant cells. The present invention thus renders it possible to obtain an improved understanding of the structure of opioid receptors and to study their mechanism of action in more detail. The present invention also renders it possible to obtain opioid receptors of very high purity and in elevated quantity, thereby permitting functional and pharmacological studies to be carried out, antibodies to be made, etc. The invention also renders it possible to prepare opioid receptor fragments of defined size, as well as all types of opioid receptor derivatives. The invention also supplies recombinant cells which express opioid receptors or opioid receptor fragments which can be used for screening ligands of these receptors (agonists, antagonists, modulators, etc.). The DNA sequences of the invention also render it possible to make probes which are capable of detecting, in biological samples, any irregularity in the expression of an opioid receptor (non-expression, mutation, polymorphism, etc.). These probes can also be used for hybridization cloning of any other cDNA encoding an opioid receptor using tissues of various origins and, in particular, of human origin, as indicated further below.

An initial subject of the invention is, therefore, a nucleotide sequence which encodes a polypeptide having an opioid receptor activity. Within the meaning of the invention, opioid receptor comprises, in particular, the delta, mu and kappa subtypes.

Preferably, the invention relates to a nucleotide sequence which encodes a polypeptide having a delta opioid receptor activity.

Still more preferably, the nucleotide sequence according to the invention is selected from among:

(a) all or part of the nucleotide sequence SEQ ID NO: 1, or of its complementary strand, (b) any sequence which hybridizes to a sequence (a) and which encodes a polypeptide having an opioid receptor activity, and (c) the sequences derived from sequences (a) and (b) on account of the degeneracy of the genetic code.

A quite specific embodiment of the invention is represented by a nucleotide sequence which comprises all or part of the nucleotide sequence SEQ ID NO: 1, or of its complementary strand.

The various nucleotide sequences of the invention may or may not be of artificial origin. They can be genomic, cDNA or RNA sequences, hybrid sequences, or synthetic or semi-synthetic sequences. These sequences can be obtained, for example, by screening DNA libraries (cDNA library or genomic DNA library) with probes which are developed on the basis of the sequence SEQ ID NO: 1. Such libraries can be prepared from cells of different origins using standard molecular biological techniques which are known to the person skilled in the art. The nucleotide sequences of the invention can also be prepared by chemical synthesis, in particular using the phosphoramidite method, or else using mixed methods including chemical or enzymic modification of sequences which are obtained by screening libraries.

The nucleotide sequences of the invention may be used for producing opioid polypeptides. The term opioid polypeptide denotes any polypeptide having an opioid receptor activity, and any fragment or derivative of such a polypeptide. In order to produce opioid polypeptides, that part encoding the said polypeptide is generally placed under the control of signals which enable it to be expressed in a host cell. The choice of these signals (promoters, terminators, etc.) can vary depending on the host cell employed. To this end, the nucleotide sequences of the invention can be part of a vector, which can be autonomously replicating or integrating. More specifically, autonomously replicating vectors can be prepared using sequences which ensure autonomous replication in the chosen host. As regards integrating vectors, these can be prepared, for example, using sequences which are homologous with certain regions of the genome of the host, thereby allowing integration of the vector to take place by homologous recombination. The host cells which can be used for producing opioid polypeptides of the invention by the recombinant route are eukaryotic hosts as well as prokaryotic hosts. The suitable eukaryotic hosts which may be cited are animal cells, yeasts or fungi. In particular, as regards yeasts, those of the genera Saccharomyces, Kluyveromyces, Pichia, Schwanniomyces or Hansenula may be cited. As regards animal cells, those which may be cited are COS, CHO, C127 and NIH-3T3 cells, etc. Those fungi which may be cited more specifically are Aspergillus ssp. or Trichoderma ssp. Preference is given to employing the following bacteria E. coli, Bacillus or Streptomyces as prokaryotic hosts.

The nucleotide sequences of the present invention can also be used in the pharmaceutical sphere, either for preparing antisense sequences which can be used within the scope of gene therapy, or, once again, for preparing probes which render it possible to detect, by hybridization experiments, expression of opioid receptors in biological samples, and to demonstrate genetic anomalies (polymorphism or mutations), or aberrant expressions.

Inhibition of the expression of certain genes by antisense sequences has turned out to be a promising strategy for controlling gene activity. Antisense sequences are sequences whose transcription product is complementary to the coding strand of a given gene and is, for this reason, capable of specifically hybridizing to the transcribed mRNA, thereby inhibiting its translation into protein. Consequently, the invention relates to antisense sequences which are capable of at least partially inhibiting the production of opioid polypeptides as previously defined. Such sequences can consist of all or part of the nucleotide sequences defined above. Generally, they are sequences, or fragments of sequences, which are complementary to sequences encoding the peptides of the invention. Such sequences can be obtained from the sequence SEQ ID NO: 1, by means of fragmentation, etc., or by means of chemical synthesis.

As indicated above, the invention also permits synthetic or non-synthetic nucleotide probes to be prepared which are capable of hybridizing to the nucleotide sequences defined above which encode opioid polypeptides of the invention, or to the corresponding mRNAs. Such probes can be employed in vitro as a diagnostic tool for detecting expression of an opioid receptor, or else for detecting gene anomalies (faulty splicing, polymorphism, point mutations, etc.). In view of the numerous activities of the endogenous ligands of opioid receptors, the probes of the invention can thus render it possible to identify neurological, cardiovascular or psychiatric affections. These probes can also be used for detecting homologous nucleic acid sequences, which encode opioid polypeptides as previously defined, in, and isolating them from, other cellular sources, preferably cells of human origin. Although the present application is more specifically illustrated by a receptor of the delta type, biochemical and immunological studies described in the literature clearly indicate that the opioid receptors possess a significant degree of homology (same molecular weights, crossreactivity with the same antibodies, etc.). The probes of the invention generally comprise at least 10 bases, and they can comprise up to the whole of the SEQ ID NO: 1 sequence, or of its complementary strand. Preferably, these probes are labelled prior to being used. For this purpose, use can be made of various techniques know to the person skilled in the art (radioactive labelling, enzymic labelling, etc.). The hybridization conditions under which these probes can be used are indicated in the general cloning techniques below as well as in the examples.

The invention also relates to any polypeptide which results from the expression of a nucleotide sequence as previously defined. Preferably, the polypeptide is one which comprises all or part of the peptide sequence SEQ ID NO: 2, or of a derivative thereof.

Within the meaning of the present invention, the term derivative denotes any molecule which is obtained by genetic and/or chemical modification of the peptide sequence SEQ ID NO: 2. Genetic and/or chemical modification is to be understood to mean any mutation, substitution, deletion, addition and/or modification of one or more residues. Such derivatives can be generated for different purposes, such as, in particular, that of increasing the affinity of the peptide for its ligand(s), that of improving its levels of production, that of increasing its resistance to proteases, that of increasing and/or modifying its activity, or that of conferring on it novel pharmacokinetic and/or biological properties. Examples of derivatives which result from an addition and which may be cited are chimeric polypeptides which comprise an additional heterologous part which is linked to one end. The term derivative also encompasses polypeptides which are homologous with the SEQ ID NO: 2 polypeptide, which are is derived from other cellular sources, in particular cells of human origin, or from other organisms, and which possess an activity of the same type. Such homologous polypeptides may be obtained by means of hybridization experiments as described in the examples.

Preferably, the polypeptides of the invention are polypeptides which possess the ability to bind morphine (mu type receptor), enkephalin (delta type receptor) or dynorphin (kappa type receptors). Still more preferably, the polypeptides are those which possess the ability to bind enkephalin (delta type receptor). Still in accordance with a preferred embodiment, the polypeptides of the invention are capable of being recognized by antibodies which recognize the complete SEQ ID NO: 2 peptide sequence. Antibodies of this nature can be generated by any technique known to the person skilled in the art, using the polypeptides described in the present application as antigens.

As indicated in the examples, these polypeptides can be expressed in different cell types in order to form functional opioid receptors.

The polypeptides of the invention can be obtained by the expression of a nucleotide sequence as described above in a host cell, by chemical synthesis on the basis of the SEQ ID NO: 2 sequence, using the techniques known to the person skilled in the art, or by a combination of these techniques.

The invention also relates to recombinant cells which are able to express, at their surface, a polypeptide having an opioid receptor activity. These cells may be obtained by introducing a nucleotide sequence as defined above and then culturing the said cells under conditions for expressing the said sequence.

The recombinant cells according to the invention can be either eukaryotic cells or prokaryotic cells. Suitable eukaryotic cells which may be cited are animal cells, yeasts or fungi. Those yeasts which may, in particular, be cited are yeasts of the genera Saccharomyces, Kluyveromyces, Pichia, Schwanniomyces or Hansenula. Those animal cells which may be cited are COS, CHO, C127 and NIH-3T3 cells, etc. Those fungi which may more specifically be cited are Aspergillus ssp, or Trichoderma ssp. Preference is given to employing the following bacteria as prokaryotic cells: E. coli, Bacillus or Streptomyces. The cells which are thus obtained may be employed for measuring the ability of different molecules to behave as ligands or as modulators of the activity of the opioid receptors. More specifically, they may be employed in this way in a procedure for detecting and isolating ligands or modulators of opioid receptor activity, and, more preferably, agonists and antagonists.

The invention also relates, therefore, to a procedure for detecting and/or isolating ligands of the opioid receptors, according to which the following steps are carried out:
- a molecule, or a mixture containing different molecules, which may not have been identified, is brought into contact with a recombinant cell as described above, which cell expresses, at its surface, a polypeptide having an opioid receptor activity, under conditions which permit interaction between the said polypeptide and the said molecule, if the latter possesses an affinity for the said polypeptide, and
- the molecules bound to the said polypeptide are detected and/or isolated.

In a specific embodiment, this procedure of the invention is adapted for detecting and/or isolating agonists and antagonists of enkephalin for the delta opioid receptors.

The invention also relates to a procedure for detecting and/or isolating modulators of the opioid receptors, according to which the following steps are carried out:
- a molecule, or a mixture containing different molecules, which may not have been identified, is brought into contact with a recombinant cell as described above, which cell expresses, at its surface, a polypeptide having an opioid receptor activity, in the presence of the endogenous ligand of the said receptor, under conditions which permit interaction between the said polypeptide and its ligand, and
- the molecules which are capable of modulating the activity of the ligand on the said polypeptide are detected and/or isolated.

In a specific embodiment, this procedure of the invention is adapted for detecting and/or isolating modulators of the activity of enkephalin on the delta opioid receptors.

The invention also relates to the use of a ligand or of a modulator which is identified and/or obtained according to the procedure described above as a medicament. This is because such ligands or modulators can render it possible to treat certain affections which are linked to the opioid receptors. Specifically, since the opioid receptors mediate an analgesic effect, agonists of these receptors can be used to diminish pain sensations. Furthermore, since these receptors are mediators of the effects of opium derivatives, their antagonists can be employed within a disintoxication treatment.

The invention also relates to any medicament which includes, as active principle, at least one molecule which acts on a receptor of the invention. Preferably, the molecule is a ligand or a modulator which is identified and/or isolated according to the previously described procedure.

Other advantages of the present invention will be apparent from reading the following examples, which are to be regarded as illustrative and not limiting.

Table 1: Pharmacological Profile of the K56 Receptor. The results relate to competition experiments for the binding of $^3$H-DTLET to the membranes of Cos-1 cells expressing the K56 receptor transiently. The IC50 values (corresponding to the ligand concentration which is necessary in order to displace 50% of the bound $^3$H-DTLET) were determined experimentally and converted into Ki in accordance with the following equation: Ki=IC50/(1+L/Kd), in which L is the concentration of $^3$H-DTLET and Kd is the dissociation constant of the $^3$H-DTLET. Each value represents the mean of 3 independent experiments.

General Cloning Techniques

The standard methods used in molecular biology, such as preparative extractions of plasmid DNA, centrifugation of plasmid DNA in a caesium chloride gradient, electrophoresis on agarose or acrylamide gels, purification of DNA fragments by electroelution, extraction of proteins with phenol or with phenol/chloroform, precipitation of DNA in a saline medium using ethanol or isopropanol, transformation into *Escherichia coli*, etc., are well known to the person skilled in the art and are abundantly described in the literature [Maniatis T. et al., "Molecular Cloning, a Laboratory Manual", Cold Spring Harbor Laboratory, Cold Spring Harbor, N.Y., 1982; Ausubel F. M. et al., (eds), "Current Protocols in Molecular Biology", John Wiley & Sons, New York, 1987].

For ligations, the DNA fragments are separated according to their size by means of electrophoresis in agarose or acrylamide gels, extracted with phenol or with a phenol/chloroform mixture, precipitated using ethanol, and then incubated in the presence of phage T4 DNA ligase in accordance with the supplier's recommendations.

The protruding 5' ends are filled in using the Klenow fragment of *E. coli* DNA polymerase I in accordance with the supplier's specifications. The protruding 3' ends are destroyed in the presence of phage T4 DNA polymerase, which is employed in accordance with the manufacturer's recommendations. The protruding 5' ends are destroyed by careful treatment with S1 nuclease.

In vitro site-directed mutagenesis using synthetic oligodeoxynucleotides is carried out in accordance with the method developed by Taylor et al. [Nucleic Acids Res. 13 (1985) 8749-8764].

Enzymic amplification of DNA fragments is carried out using the technique termed PCR [polymerase-catalysed chain reaction, Saiki R. K. et al., Science 230 (1985) 1350-1354; Mullis K. B. and Faloona F. A., Meth. Enzym. 155 (1987) 335-350].

The nucleotide sequences are verified using the method developed by Sanger et al. [Proc. Natl. Acad. Sci. USA, 74, (1977) 5463-5467].

The stringency conditions for the hybridization experiments are based on Maniatis T. et al., as cited above.

1. Isolation of the Mouse Delta Opioid Receptor

This example describes the isolation of the clone K56, encoding the mouse delta opioid receptor, by means of screening a cDNA library by expression cloning.

1.1. Construction of the Library

A cDNA library was constructed from the hybridoma NG108-15 (Klee, W. A. and Nirenberg, M. (1974) Proc. Natl. Acad. Sci. USA 71, 3474-3477) using the mammalian transient expression vector pCDMB (Aruffo, A. and Seed, B.

(1987) Proc. Natl. Acad. Sci. USA 84, 8573-8577). For this purpose, NG108-15 cells [supplied by B. Foucaud (URA 1836, Faculté de Pharmacie, Strasbourg, France)] were harvested at 50% confluence, the RNA was extracted from these cells by precipitation in the presence of lithium chloride and urea (Auffray et al., (1980) Eur. J. Biochem. 107, 303-314), and the polyA RNAs were purified on an oligo (dT) column (Pharmacia). The cDNA library was then constructed, using *E. coli* as the host, in the vector pCDM8 (supplied by B. Seed, Massachusetts General Hospital, USA) using the technique described by Kieffer (1991, Gene 109, 115-119). Approximately 300,000 transformants were cultured for one night in Petri dishes (16 cm) at a density of 3000 colonies per dish. The colonies were then transferred to a selective LB medium. Half of the suspension which was obtained was preserved in frozen form at −80° C. in the presence of 30% glycerol, and the remainder was used for preparing plasmid DNA by the alkaline lysis technique (Sambrook, J., Fritsch, E. F. & Maniatis, T. (1989) Molecular Cloning: A Laboratory Manual (Cold Spring Harbor Lab., Cold Spring Harbor, N.Y.), 2nd Ed.).

One tenth of the plasmid DNA from each batch was independently transfected into Cos-1 cells (ATCC CRL/1650) using the DEAE dextran technique. The best efficiency of transfection (up to 20% transfected cells) was obtained using the following protocol: monolayer Cos-1 cells were cultured in 6 cm dishes, at a density of $2.10^5$ cells per dish, in DEM (Dulbecco's Modified Eagle Medium), in the presence of 10% foetal calf serum (FCS) and under 5% $CO_2$. After 16 hours at 37° C., the cells were washed 2 times in a phosphate buffer (PBS, pH 7.4), and incubated at 37° C. for 1 hour together with a solution consisting of 1-10 µg of DNA, 0.25 mg/ml of DEAE dextran (Pharmacia), 10 mM Tris-HCl, pH 7.4, in 2 ml of DMEM. The cells were then treated with 10% glycerol in 2 ml of DMEM for 3 minutes, rapidly diluted with 5 ml of PBS and washed 2 times with PBS. Finally, the cells were incubated at 37° C. for 5 hours in DMEM medium containing 10% FCS and 0.1 mM chloroquine, washed once in DMEM medium containing 10% FCS, and then cultured for 72 hours in this medium.

1.2. Screening by Expression

The transfected Cos-1 cells described in 1.1. above were tested for their ability to bind the following peptide: Tyr-D-Thr-Gly-Phe-Leu-Thr (DTLET), which was labelled with tritium (61 Ci/mmol, CEA, Saclay, France). The use of a ligand hating a weak specific activity in such a screening test had not previously been described. The cells in monolayer were washed twice in the presence of PBS which was supplemented with 0.5% bovine serum albumin (BSA), and then incubated at 37° C. for 35 minutes in the presence of PBS supplemented with 0.5% BSA and containing 1 nM $^3$H-DTLET (2 ml), which corresponds to the Kd of the native receptors. The dishes were cooled on ice for 5 minutes, and the cells were washed 4 times with PBS supplemented with 0.5% cooled BSA. The cells were then solubilized in 1.5 ml of 1% SDS, added to 7 ml of scintillation liquid and counted (LS6000SC, Beckman).

The positive batches were fractionated by diluting an aliquot of stock, frozen in glycerol, in a selective medium, and then spreading the suspension on nitrocellulose membranes laid on agar plates. Following overnight culture, membrane fragments were cut out in order to isolate batches of independent colonies. These various colonies were transferred into 10 ml of selective LB medium and cultured up to an $OD_{600}$ nm of 0.5. An aliquot was frozen in glycerol and the remainder was used to prepare plasmid DNA and transfect Cos-1 cells as described above.

A first positive batch was detected which produced a signal which exceeded background by 10%. This batch was divided into 40 batches of 250 clones. These batches were tested once again for their ability to bind $^3$H-DTLET. In order to assess the specificity of the bound $^3$H-DTLET, the clones which had thus been fractionated were incubated in the presence of cold naloxone, an opioid antagonist. Several clones produce a signal which surpasses background by 20% and disappears in the presence of naloxone. One of these was subdivided twice (40 batches of 30 clones and then 90 individual clones), leading to a single clone, designated K56, which confers a strong $^3$H-DTLET-binding activity on Cos-1 cells. In particular, the signal which is obtained is 6-fold greater than background, is sensitive to naloxone, and is dependent on the concentration of $^3$H-DTLET.

2. Study of the Structure of the Delta Opioid Receptor Carried by Clone K56

Clone K56 contains an insert of approximately 2.2 kb, the sequences of both strands of which were determined using the dideoxynucleotide technique (sequenase kit, US Biochemicals).

The sequence thus obtained corresponds to the SEQ ID NO: 1 sequence. It demonstrates that the isolated cDNA carries an open reading frame of 1174 bp encoding a protein which consists of 371 amino acids (SEQ ID NO: 2) and has a calculated molecular weight of 40810 daltons (the translation initiation site was assigned to the ATG codon at position 59 in this ORF). Furthermore, the hydrophobicity analysis shows that this protein carries 7 transmembrane (Tm) hydrophobic domains, a feature encountered in the members of the family of receptors coupled to G proteins. Furthermore, the conserved residues in these proteins are also present in the K56 protein, namely:

a proline in the Tm domains IV, V, VI and VII,
a tryptophan in the Tm domains IV and VI, and in the first extracellular loop,
the consensus sequences GNxxV (Tm I); LAxAD (Tm II); DRY (2nd intracellular loop; and NPxxY (Tm VII).

Furthermore, the K56 protein possesses an Asp residue at position 128 which is equivalent to the Asp 113 residue of the β-adrenergic receptors and which might therefore be implicated in the ligand-binding site.

Finally, the sequence of the K56 protein was compared with the sequences of other proteins from the family of receptors coupled to G proteins, namely:

the β2 adrenergic receptor,
the receptor for neuromedin K,
the receptor for rhodopsin, and
the receptor for the N-formyl peptide.

The greatest degree of homology which was obtained was of 30%, including 10 gaps. This is the strongest homology obtained with the proteins of the Swissprot Data bank.

3. Pharmacological Study of the K56 Receptor

The KS56 plasmid isolated in Example 1 was used to transfect Cos-1 cells. The membranes of the transfected cells which were obtained were then prepared and tested for their ability to bind certain labelled opioid ligands.

The caesium chloride-purified plasmid K56 (plasmid pCDM8 which contains the insert of approximately 2.2 kb encoding the opioid receptor) was used to transfect Cos-1 cells (on a 10 cm plate) using the DEAE dextran technique. The control consists of cells which are transfected with the pCDM8 plasmid.

72 hours after transfection, the recombinant cells are harvested and the membranes are prepared in the following manner: the cell pellets are taken up, at 4° C., in 60 ml of 50 mM Tris-HCl, pH 7.4; 10 mM EDTA buffer, then homogenized and centrifuged at 1100 g for 10 minutes. The pellet is subsequently taken up for a second time in 30 ml of the same buffer, and homogenized and centrifuged. The 2 supernatants are combined and centrifuged at 110,000 g for 15 minutes. The membranous pellet is then taken up in 5 ml of the same buffer, aliquoted and stored at −80° C. Saturation binding experiments and competition experiments were then carried out on these membranes in the presence of various ligands. For this purpose, the membrane samples (15-30 μg of proteins) were incubated at 37° C. for 30 minutes in the presence of $^3$H-DTLET, with or without competitor, in a final volume of 1 ml of 50 mM Tris-HCl (pH 7.4); 10 mM EDTA buffer. The reaction is subsequently stopped by in-vacuo filtration through Whatman GF/B filters, followed by rinsing 3 times with 3 ml of cold buffer. The Ki values were obtained using the equation of Cheng and Prussof: Ki=IC50/(1+L/Kd). The radioactivity was measured using a β counter.

3.1. Affinity of DTLET for Transfected Cos-1 Cells.

The affinity of DTLET for transfected Cos-1 cells was determined using the general conditions of operation described above. The membranes were incubated in the presence of increasing concentrations of $^3$H-DTLET and in the absence (total binding) or in the presence (non-specific binding) of $10^{-6}$ M (−) naloxone. The specific binding corresponds to the difference between total binding and non-specific binding. The results which are obtained demonstrate that high specific binding is observed in the case of the membranes from Cos-1 cells which are transfected with plasmid K56, whereas it is negligible in the case of the membranes from control cells (Cos-1 cells transfected with plasmid pCDM8) (see FIG. 1). The binding to the membranes of NG 108-15 cells, which express the delta opioid receptor naturally, is presented as a comparison.

Figure 1:
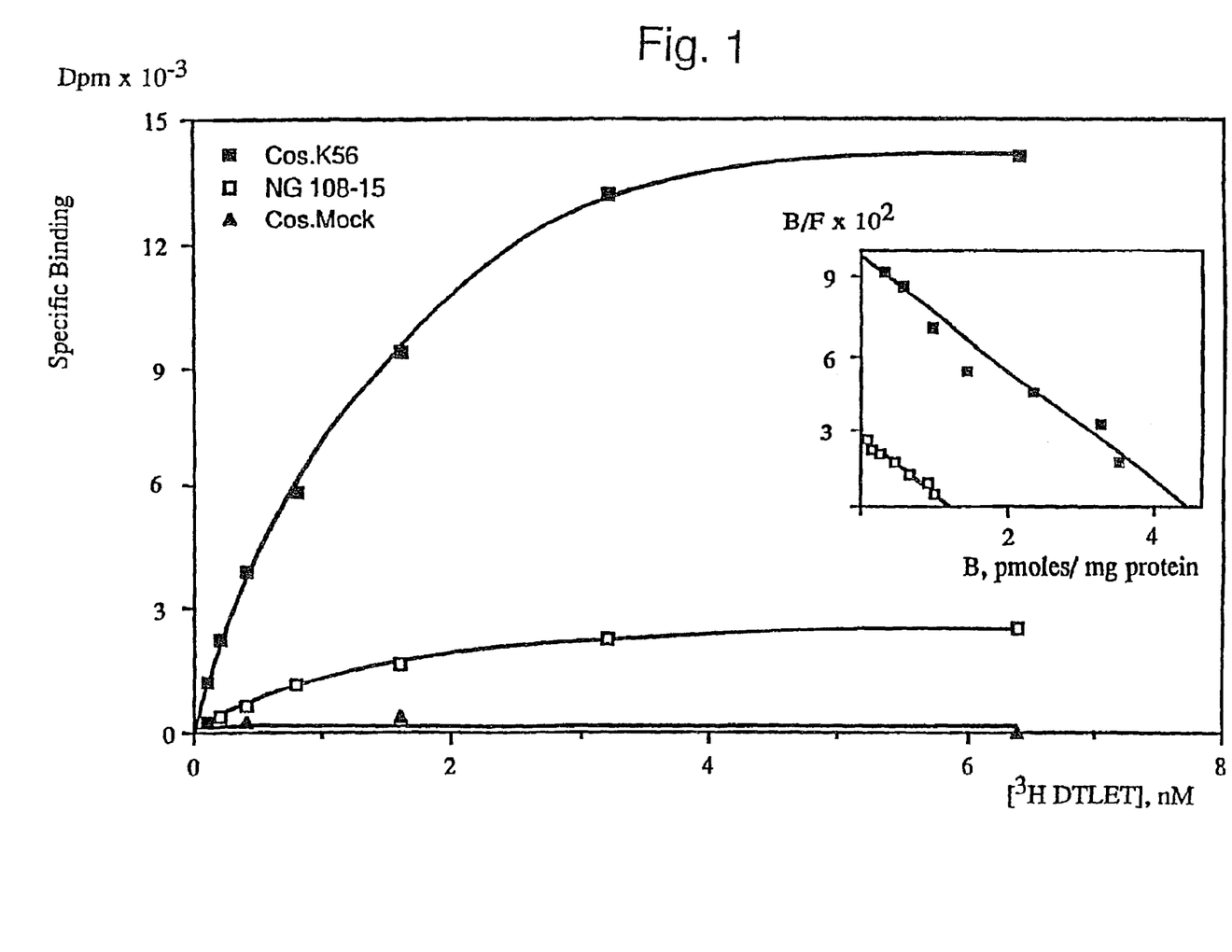
FIG. 1: Curve of the binding of $^3$H-DTLET to the membranes of Cos-1 cells expressing the K56 receptor. The membranes were incubated with increasing concentrations of ligand, with or without 1 μM of naloxone (–). The specific binding is depicted. The inset depicts a Scatchard analysis of the results.

The Scatchard analysis of the specific binding shows the presence of a single class of receptors, with an apparent dissociation constant, Kd=1.4 nM; and a Bmax of between 3.9 and 6.4 pmol per mg of protein, depending on the membrane preparations (FIG. 1). Taking into account the efficiency of transfection (approximately 10%), the level at which the opioid polypeptides of the invention are expressed in the transfected Cos-1 cells can be estimated to be $5.10^6$ molecules/cell.

3.2 Competition Experiments.

For the competition experiments, the $^3$H-DTLET was used at a concentration of 1 nM in the presence of increasing concentrations of unlabelled competitors. The unlabelled competitors which were used are the following:

DADLE: [D-Ala$^2_1$, D-Leu$^5$]-enkephalin, Sigma
DPDPE: cyclic [D-penicillamine$^2$, D-penicillamine$_5$]-enkephalin, Sigma
DAGO: [D-Ala$^2$, MePhe$^4$, Gly-ol$^5$]-enkephalin, Sigma
U50488: trans-(±)-3,4-dichloro-N-methyl-N-(2-[1-pyrrolidinyl]cyclohexyl)benzeneacetamide, Sigma
(+)- and (−)-naloxone,
levorphanol and dextrorphan,
bremazocine, and
etonitazene.

Figure 2:
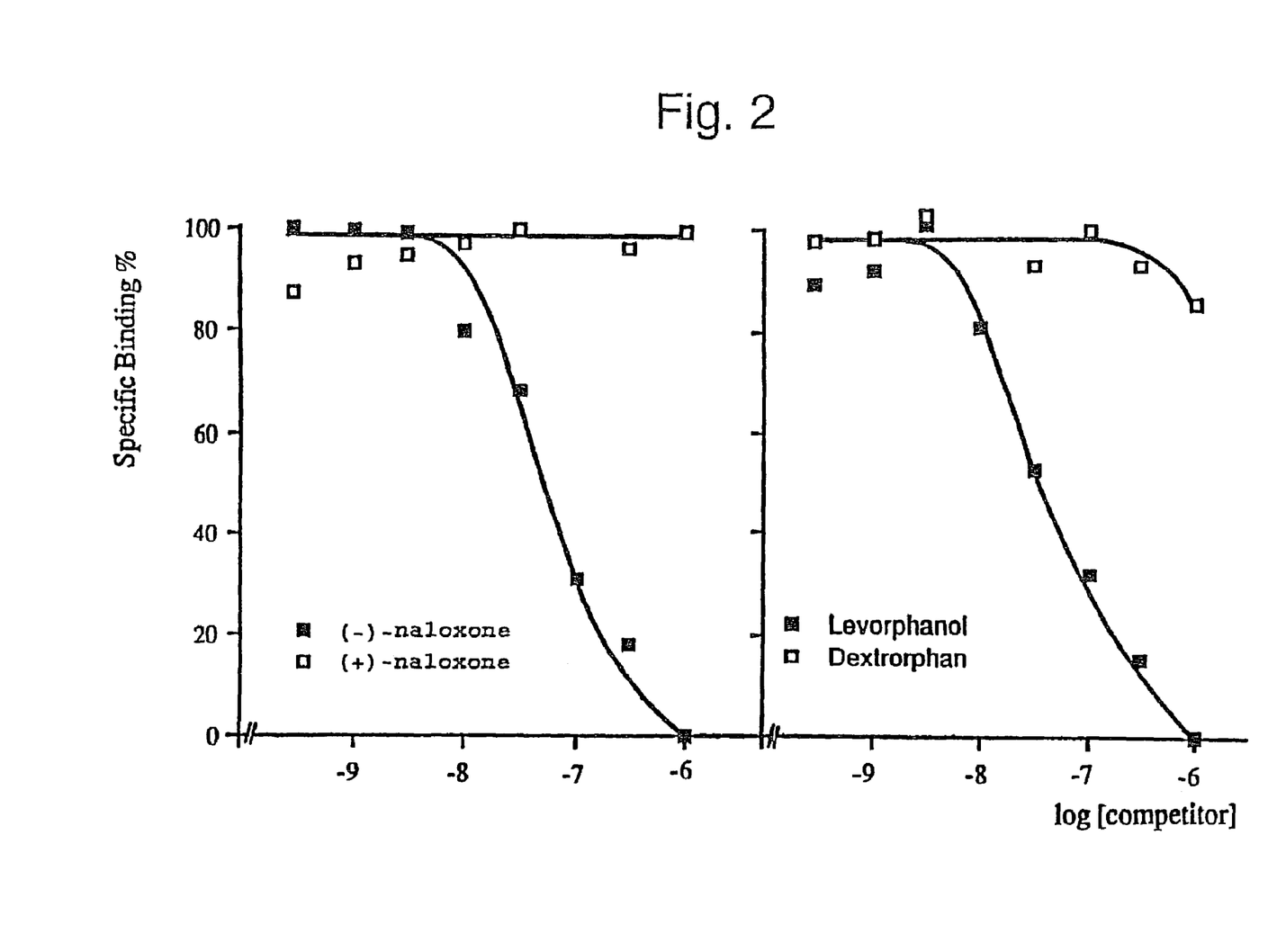
FIG. 2: Curve of the binding of $^3$H-DTLET to the membranes of Cos-1 cells expressing the K56 receptor, in the presence of increasing concentrations of competitors.

The opioid receptors are very stereoselective. Levorphanol and (−)-naloxone are known to bind the opioid receptors with a high degree of affinity, whereas the enantiomers dextrorphan and (+)-naloxone, respectively, do not bind at all, irrespective of the subtype of receptor which is studied. Competition experiments which were conducted with DTLET in the presence of the 2 pairs of ligands demonstrate that (i) (+)-naloxone is not a competitor, (ii) 1 μM dextrorphan induces mild inhibition, which is in agreement with the findings for this product which indicate that while it can bind to opioid receptors, it does so with an affinity which is 1000 times less than that of levorphanol; (iii) the 2 (−) enantiomers possess inhibition constants, Ki, which correspond to those described in the literature for a δ opioid receptor (29.5 nM for (−)-naloxone and 20.9 nM for levorphanol) (see FIG. 2 and Table 1).

Figure 3:
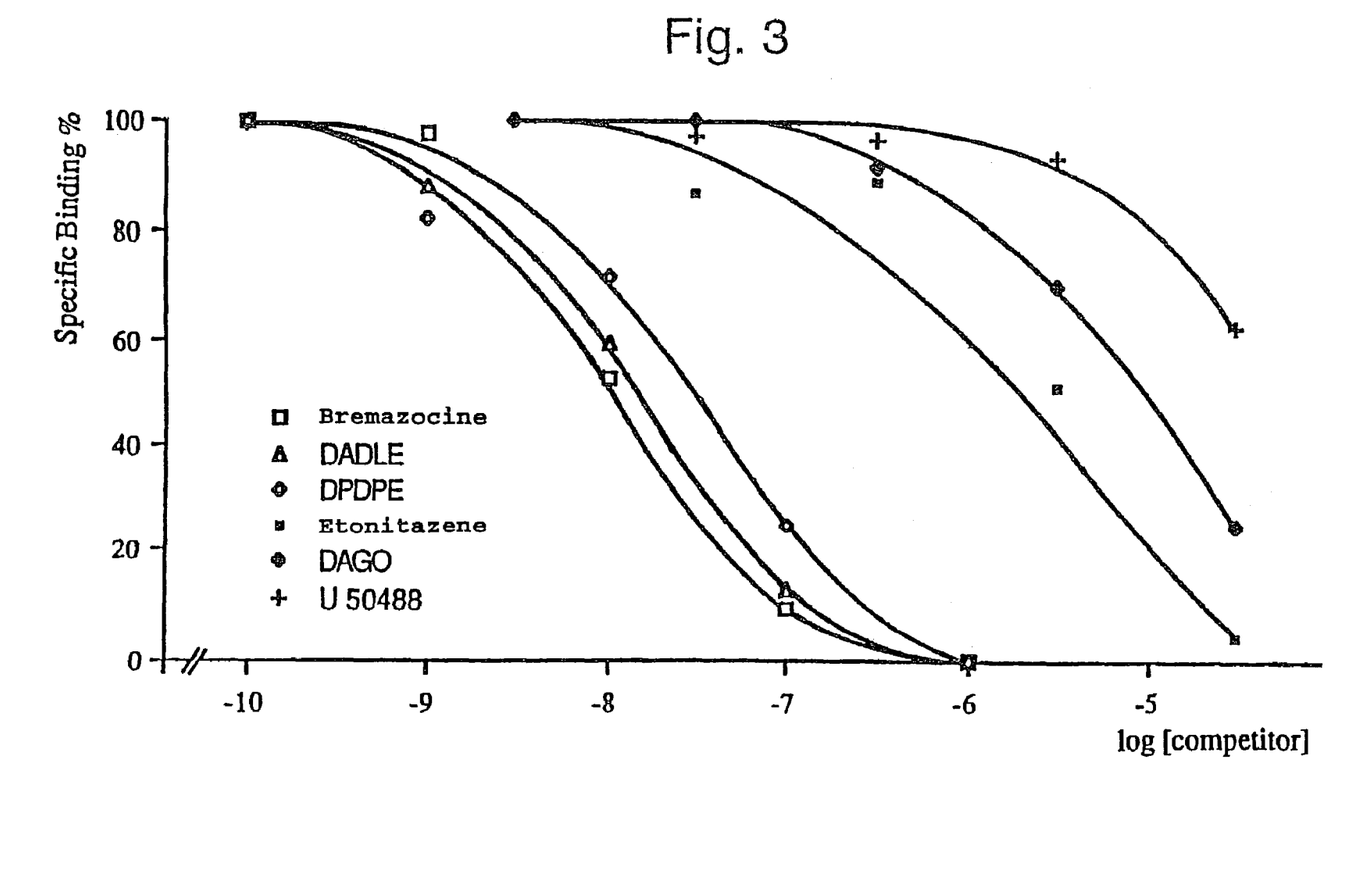
FIG. 3: Curve of the binding of $^3$H-DTLET (1 nM) to the membranes of Cos-1 cells expressing the K56 receptor, in the presence of increasing concentrations of competitors.

Furthermore, the experiments which were carried out with the other ligands which have been mentioned demonstrate that (see FIG. 3 and Table 1):

the δ agonists, DADLE and DPDPE, as well as the non-selective agonist bremazocine, are the most efficient competitors, with Ki values of 6.2, 10.9 and 5.7 nM, respectively;

the μ agonists, etonitazene and DAGO are weak ligands, with Ki values of 1800 and 5050 nM, respectively; and the κ agonist, U50488 is the least efficient competitor, with a Ki of 39,100 nM.

The order of efficiency of these different ligands confirms that the K56 receptor is to be classified as a delta opioid receptor. These results also demonstrate that the Cos-1 cells of the invention are well able to express opioid polypeptides which have binding characteristics which are comparable to those of the native receptors.

4. The Search for Homologous Sequences in Other Tissues

The nucleotide sequence SEQ ID NO: 1, or fragments thereof, can be used to detect homologous sequences in other tissues. Various techniques such as PCR, in situ hybridization, Northern blotting, etc., can be used for this purpose.

More specifically, for searching by means of PCR, the total RNAB are prepared from the different tissues under study using the technique described by Cathala et al. (DNA 2(4) (1983)). The RNAs are then subjected to reverse transcription and amplification, in the presence of reverse transcriptase, Taq polymerase and appropriate probes derived from the SEQ ID NO: 1 sequence. The products thus obtained are then transferred onto nitrocellulose filters and hybridized under varying conditions of stringency.

The homologous sequences which are detected in these experiments can, of course, then be isolated and/or amplified using standard molecular biological techniques.

5. Cloning the Human Receptor

The human receptor which is homologous to the receptor described in Example 1 was cloned by means of screening a human placental genomic library using a probe corresponding to the encoding part of the SEQ ID NO: 1 sequence. The screening was carried out by hybridizing under high stringency conditions: 5×SSC, 5× Denhardt's, 40% formamide, 0.1% SDS, 0.05% NaPPI, 100 μg/ml salmon sperm DNA, 42° C. This screening resulted in the isolation of 2 clones which contained sequences encoding the human homologue. The first contained an exon encoding the first 77 amino acids of the protein, and the second contained 2 exons, one encoding amino acids 78 to 194 and the other encoding amino acids 195 to 372. The sequence thus obtained, certain positions in which still have to be confirmed, is depicted as SEQ ID NO: 3.

TABLE 1

| Ligand | Subtype preference | PK$_i$ Cos K56 | PK$_i$ NG 108-15 |
|---|---|---|---|
| Bremazocine | k = μ = δ | 8.25 ± 0.12 | 8.75 |
| DADLE | δ = μ >>> k | 8.22 ± 0.15 | 8.70 |
| DPDPE | δ >> μ >> k | 7.73 ± 0.48 | 8.30 |
| Levorphanol | μ >> k = δ | 7.68 ± 0.07 | nd |
| (−)-Naloxone | μ > δ = k | 7.53 ± 0.09 | nd |
| Etonitazene | μ >>> δ | 5.75 | 6 |
| DAGO | μ >> δ > k | 5.21 ± 0.17 | 5.65 |
| U 50488 | k >>> μ > δ | 4.35 ± 0.15 | 4.24 |

The invention claimed is:

1. An isolated polypeptide comprising SEQ ID No. 4.

2. An isolated polypeptide consisting of SEQ ID No. 4.

* * * * *